United States Patent [19]

Ogunbiyi et al.

[11] Patent Number: 4,614,549

[45] Date of Patent: Sep. 30, 1986

[54] METHOD FOR ENZYMATIC CLEANING AND DISINFECTING CONTACT LENSES

[75] Inventors: Lai Ogunbiyi, Fairport; Thomas M. Riedhammer, Rochester; Francis X. Smith, Walworth, all of N.Y.

[73] Assignee: Bausch & Lomb Incorporated, Rochester, N.Y.

[21] Appl. No.: 690,364

[22] Filed: Jan. 9, 1985

Related U.S. Application Data

[63] Continuation of Ser. No. 545,314, Oct. 24, 1983, abandoned.

[51] Int. Cl.$^4$ .............................................. B08B 3/10
[52] U.S. Cl. ........................................ 134/19; 134/30; 134/42; 252/174.12; 422/28; 435/264
[58] Field of Search ............................. 134/30, 42, 19; 252/174.12, DIG. 12; 435/264; 422/28

[56] References Cited

U.S. PATENT DOCUMENTS

| | | | |
|---|---|---|---|
| 3,574,120 | 4/1971 | Siebert et al. | 252/132 |
| 3,590,121 | 6/1971 | Schiff | 424/50 |
| 3,855,142 | 12/1974 | Pader et al. | 252/135 |
| 3,910,296 | 10/1975 | Karageozian et al. | 134/42 |
| 3,962,107 | 6/1976 | Levin et al. | 252/100 |
| 4,011,169 | 3/1977 | Diehl et al. | 252/95 |
| 4,021,377 | 5/1977 | Borchert et al. | 252/546 |
| 4,048,122 | 9/1977 | Sibley et al. | 134/2 |
| 4,065,324 | 12/1977 | Rankin | 134/30 |
| 4,096,870 | 6/1978 | Manfuso, Jr. | 134/28 |
| 4,104,187 | 8/1978 | Sibley et al. | 134/42 |
| 4,126,587 | 11/1978 | Sibley et al. | 252/541 |
| 4,155,868 | 5/1979 | Kaplan et al. | 252/95 |
| 4,285,738 | 8/1981 | Ogata | 134/42 |
| 4,395,346 | 7/1983 | Kleist | 134/42 |

FOREIGN PATENT DOCUMENTS

| | | |
|---|---|---|
| 0005131 | 10/1979 | European Pat. Off. |
| 2854278 | 3/1980 | Fed. Rep. of Germany |
| 50-64303 | 5/1975 | Japan ............ 134/42 |
| 1577524 | 10/1980 | United Kingdom |

OTHER PUBLICATIONS

Chemical Abstracts, vol. 73, No. 14, Oct. 5, 1970, No. 73267j, "Effect of Some Proteases on Bovine Crystalline Lens; in vitro Study".

Arch. Ophthalmol. vol. 103, Jan. 1985.

Lo, Journal of the American Optometric Association, vol. 40, No. 11, pp. 1106–1109, Nov. 1969.

*Primary Examiner*—Peter Hruskoci
*Attorney, Agent, or Firm*—Bernard D. Bogdon; Dewitt M. Morgan; Annette M. Sansone

[57] ABSTRACT

Contact lenses are both cleaned and disinfected in aqueous solutions of proteolytic enzyme in a single-step by heating to a temperature of between 60° and 100° C. The cleaning and disinfecting process which may be conducted in one hour or less performs favorably against conventional methods wherein cleaning and disinfecting are conducted separately over a time period of up to twelve hours.

26 Claims, No Drawings

METHOD FOR ENZYMATIC CLEANING AND DISINFECTING CONTACT LENSES

This is a continuation of application Ser. No. 545,314, filed Oct. 24, 1983 now abandoned.

BACKGROUND OF THE INVENTION

The present invention relates to improved methods for cleaning lenses. More specifically, this invention relates to improved methods for cleaning and disinfecting contact lenses through the use of enzymatic cleaners wherein the time interval needed to complete the process can be significantly reduced thereby providing greater flexibility and convenience to the wearer.

In the normal course of wearing contact lenses, tear films and debris consisting of proteinaceous, oily and sebaceous matter have a tendency to deposit and build-up on lens surfaces. As part of the routine care regimen, hydrophilic gel lenses or soft contact lenses, for example, must be cleaned to remove these tear film deposits and debris. Otherwise, if not removed, both wettability and optical clarity of the lenses can be reduced. Because the composition of such deposits is mainly proteinaceous, enzyme cleaning solutions containing mainly proteolytic enzymes have been widely used.

Although most enzyme cleaners are generally regarded as efficacious and safe, they nevertheless have certain shortcomings which create inconveniences for the user. Heretofore, the process of cleaning contact lenses with enzymatic cleaners involved two main steps: the first consisting of the cleaning phase whereby coated lenses are soaked in the enzyme solution at ambient temperature conditions, i.e. . . . cold soaking, for a period of at least 2 hours and up to 12 hours, and occasionally, overnight to achieve effective cleaning. At the conclusion of the cleaning step, the lenses must be disinfected. Disinfection normally requires exposing the lenses to a temperature of 80° C. for at least 10 minutes. This is carried out by first immersing the lenses in a lens storage case with a second solution, such as preserved isotonic sterile saline followed by asepticizing in a heat disinfection unit. Such units have a heating cycle which normally takes about 1 hour to complete. Thus, the time needed to clean and disinfect soft contact lenses utilizing enzymatic cleaners can take up to 13 hours. Accordingly, there is a need for an abbreviated, more convenient means for cleaning contact lenses with enzyme cleaners which provides a greater degree of flexibility.

The present invention provides a less complex and more convenient regimen for enzymatic cleaning of contact lenses whereby actual cleaning and disinfection are carried out in the enzyme solution in a single step over a significantly reduced time period of 60 minutes or less. The method of present invention provides the added benefit of concurrent deactivation of the active enzymes by the time the cycle is completed. In addition to the greater convenience factor for the user, the improved methods for enzymatic cleaning are also more economic since only a single lens care solution is needed; whereas, previous methods required both a cleaning solution and another rinsing solution.

SUMMARY OF THE INVENTION

This invention relates to methods of treating contact lenses having proteinaceous tear film deposits and debris wherein the lenses are heated in aqueous solutions of a proteolytic enzyme to a temperature sufficient to disinfect the lenses and allow the enzyme to effectively clean in a single step in the same solution. During the heating phase, the lenses are heated up in the enzyme cleaning solution to temperature of less than 100° C. which are maintained for a time period, e.g. . . . usually less than 15 minutes, and then allowed to cool to room temperature.

The process of the present invention is adaptable to most enzyme products useful for cleaning contact lenses which contain proteolytic, carbolytic and lipolytic enzymes, either alone or in combination. Such enzymes include protease, amylase and lipase derived from plant, animal or microbial sources. Representative examples include such enzymes as papain and pancreatin, to name but a few. The one-step enzymatic cleaning process disclosed herein is also adaptable to cleaning solutions prepared with microbial protease and amylase derived from Bacillus and Streptomyces bacteria and Aspergillus mold.

PREFERRED EMBODIMENTS OF THE INVENTION

This invention relates to novel methods for cleaning and disinfecting contact lenses. The methods are adaptable for use with most contact lenses, including hard and soft lenses, as well as the newer hard gas permeable type contact lenses, such as described in U.S. Pat. No. 4,327,203. The invention also relates to those soft lenses generally referred to as extended-wear lenses containing 55% or more water content. The term "soft contact lens" as used herein also generally refers to those lenses which readily flex under small amounts of force and return to their original shape when that force is released. Typically, soft contact lenses are formulated from poly(hydroxyethyl methacrylate) which has been in the preferred formulations cross-linked with ethylene glycol dimethacrylate. For convenience purposes, this polymer is generally known as PHEMA. Soft contact lenses are also made from silicon polymer cross-linked, for example, with dimethyl polysiloxane. Conventional "hard contact lenses" which cover only the cornea of the eye, usually consist of poly(methyl methacrylate) cross-linked with ethylene glycol dimethacrylate.

The improved methods for cleaning and disinfecting contact lenses in the same solution in a single step are carried out by heating the lenses in an enzyme-containing solution which is both effective, safe and non-toxic. The single-step method both cleans and disinfects contact lenses usually in 60 minutes or less.

The cleaning solutions may include proteolytic, carbolytic and lipolytic enzymes, either individually or in combinations. Such enzymes include those derived from plant sources, animal sources and microorganisms, including bacteria and molds. Typical examples include, but are not limited to papain, chymopapain, pancreatin, pepsin, trypsin, chymotrypsin, protease, amylase, lipase, ficin, bromelin, streptokinase, streptodornase, etc. Protease and amylase derived from Bacillus and Streptomyces bacteria and Aspergillus mold also have been found to perform well with the single-step cleaning and disinfecting method of the present invention. Enzymatic cleaning solutions prepared principally with microbial protease and amylase and optionally, lipase are described in co-pending application Ser. No. 545,315, filed on even date herewith. Protease and amylase derived, for example, from *B. subtilis* and *Aspergillus niger* effectively remove protein and carbohydrate films resulting from eye secretions and tears without damaging lenses.

They are substantially odor-free, non-allergenic, do not require activator/stabilizer, and dissolve completely in aqueous solutions. Such bacterial enzymes are readily available, for example, from the Enzyme Development Corporation, Keyport, N.J. under the Enzeco Trademark, which includes a food grade of PROTEASE AP I. Other grades of bacterial proteases are commercially available and suitable for use in the methods described herein.

The single-step cleaning and disinfecting process is conducted by immersing the lenses in an aqueous solution of the enzyme cleaner. For purposes of the present invention—aqueous solution—includes water, but preferably solutions adjusted with tonicity agents to approximate the osmotic pressure of normal lacrimal fluids which is equivalent to a 0.9% solution of sodium chloride or 2.5% solution of glycerol. The aqueous solutions of enzymes are preferably made isotonic to avoid potential discomfort to the user of the lenses after they are cleaned, disinfected and reinserted.

The aqueous enzyme solutions preferably contain preservatives which are compatible with and do not precipitate in the presence of the enzymes, and comprise concentrations ranging from about 0.00001 to about 0.5 weight percent, and more preferably, from about 0.0001 to about 0.1 weight percent. Suitable preservatives include, but are not limited to thimerosal, sorbic acid, 1,5-pentanedial, alkyl triethanolamines, phenylmercuric salts e.g. nitrate, borate, acetate, chloride and mixtures thereof. Other germicidal compounds and salts may be used, such as salts which are soluble in water at ambient temperature to the extent of at least 0.5 weight percent. These salts include the gluconate, isothionate(2-hydroxyethanesulfonate), formate, acetate, glutamate, succinamate, monodiglycollate dimethanesulfonate, lactate, diisobutyrate and glucoheptonate.

In most instances, the aqueous enzyme cleaning and disinfecting solutions will contain various sequestering or chelating agents to bind metal ions, such as calcium, which might otherwise react with protein and collect on lens surfaces. Ethylenediaminetetraacetic acid (EDTA) and its salts (disodium) are preferred examples. Chelating agents are normally employed in amounts from about 0.1 to about 2.0 weight percent.

In addition to the tonicity agents, preservatives and chelating agents mentioned above the aqueous solutions containing the enzyme(s) may also include buffering agents and surfactants. Suitable buffers include, for example, sodium or potassium citrate, citric acid, boric acid, sodium borate, sodium bicarbonate and various mixed phosphate buffers, including combinations of $Na_2HPO_4$, $NaH_2PO_4$ and $KH_2PO_4$. Generally, buffers may be used in amounts ranging from about 0.5 to about 2.5%, and more preferably, from about 0.1 to 1.5% by weight.

In some instances, it may be desirable to include in the aqueous enzyme cleaning solutions surface active agents, preferably neutral or non-ionic types for their supplemental cleaning and conditioning properties. Surface active agents may be used generally in amounts ranging up to 15 weight percent. Examples of surfactants suitable for use in conjunction with the enzymes include polyethylene glycol esters of fatty acids e.g. coconut, polysorbate, polyoxyethylene, polyoxypropylene ethers of higher alkanes ($C_{12}$–$C_{18}$). Examples of preferred surfactants includes polysorbate 20 (available under the trademark Tween 20), polyoxyethylene (23), lauryl ether (Brij. ® 35), polyoxyethylene (40) stearate (Myrj. ®) polyoxyethylene (25), propylene glycol stearate (Atlas ® 12).

Also included within the group of surfactants noted above is a group of nonionic surface active agents consisting of a poly(oxypropylene)-poly(oxyethylene) adduct of ethylene diamine having a molecular weight from about 7500 to about 27,000 wherein at least 40 weight percent of said adduct is poly(oxyethylene) has been found to be particularly useful in cleaning and conditioning both soft and hard contact lenses in amounts from about 0.01 to about 15 weight percent. Such surfactants are available from BASF-Wyandotte under the trademark—Tetronic.

Lenses are covered with the above aqueous enzyme solutions, usually in a lens case, are heated to a temperature which will disinfect and allow cleaning in one-step in the same solution. This is preferably carried out by a cycle consisting of a heating phase and a cooling phase. The heating phase consists of gradually elevating the temperature of the solution from ambient temperature to a maximum temperature of usually less than 100° C., and more specifically, from about 60° to about 85° C. When the maximum temperature has been reached the temperature is maintained usually for not more than 20 minutes, and more often for about 5 to about 15 minutes.

Although the precise mechanism for the cleaning reaction remains uncertain the activity of the enzyme for example, in denaturing and removing protein from lens surfaces is believed to be enhanced as the temperature rises. Likewise, when the maximum temperature has been reached during the heating phase and maintained for about 10 minutes, this action operates automatically to inactivate the enzyme terminating the cleaning process while simultaneously disinfecting the lenses. At the conclusion of the heating phase the cooling phase commences whereby the cleaned and disinfected lenses and the inactivated cleaning solution are allowed to cool to ambient temperature. The lenses are then ready for reinserting onto the eyes.

The process is most conveniently conducted with any of the well known commercially available contact lens heat disinfecting units, such as those available from Bausch & Lomb under the trademark Aseptron. Such heat disinfecting units, in most instances, can be adapted to the single-step process. They have temperature profiles which typically include heating up to 80° C. which temperature is maintained for approximately 10 minutes, the entire cycle taking about 60 minutes. Temperature profiles of heat units can be modified depending on the type of lens, where for instance, extended wear type contact lenses may be treated to even more abbreviated cleaning and disinfecting cycles and at lower temperature ranges to minimize the potential for both physical damage, discoloration, etc.

The following specific examples demonstrate the methods of the subject invention. It is to be understood that these examples are for illustrative purposes only and do not purport to be wholly definitive as to conditions and scope.

EXAMPLE I

In order to evaluate the performance of the single-step cleaning and disinfecting method and compare it to the conventional two-step method, the following enzyme formulations are prepared:

Water Soluble, Non-Effervescent Tablet

Water-soluble, non-effervescent tablets are prepared with each tablet containing about 25 to 30 mg of PROTEASE AP I enzyme commercially available under the Enzeco trademark from Enzyme Development Corporation, Keyport, N.J. The enzyme is derived from *B. subtilis* and contains principally protease and α-amylase activity. The protease activity is approximately 53 casein units/mg. The enzyme is stable at a pH of between 5.0 and 10.0.

The enzyme powder is first granulated with a sufficient amount of a pharmaceutical grade polyethylene glycol (4000) or other suitable binder and lubricant. The granulated fines are then formed into compressed tablets.

Water-Soluble Effervescent Tablet

Effervescent enzyme cleaning tablets are made by preparing an effervescent excipient containing sodium bicarbonate, citric acid and sodium chloride in a weight ratio of 3:1:1. Each of the salts is finely ground separately in a mortar and then mixed together with the aid of a mortar and pestle. A small amount of distilled water e.g. . . . <0.5 ml is added to the mixture and further blended to initiate molecular interaction of the salts. The mixture is spread evenly on a glass plate and placed in a vacuum oven for 2 to 3 hours at 60° C. The mixture is then finely ground in a mortar and blended with Enzeco Protease AP I enzyme powder in a ratio of excipient to enzyme of 2:1 to provide about 25 to 30 mg of enzyme per tablet. Tablets are then made by compressing at 2500 psig.

EXAMPLE II

A clear artificial tear solution is prepared consisting of 0.2 grams of lysozyme/100 ml of electrolyte. The electrolyte is a stock solution prepared from sodium bicarbonate 2.2 gpl, sodium chloride 7 gpl, calcium chloride 0.0005 gpl and potassium chloride 1.5 gpl.

Eight (8) polymacon soft contact lenses commercially available from Bausch & Lomb under the registered trademark Soflens are microscopically inspected before coating with the lysozyme solution. The lenses are then soaked in the lysozyme solution for 30 to 60 minutes at room temperature. The lenses are then placed individually into the wells of Lensgard ® carrying cases and placed into Bausch & Lomb Aseptron ® heat units in order to denature the lysozyme protein. This procedure is repeated for 10 cycles on the same lenses.

Before initiating the cleaning process, light transmission readings for each of the lenses is measured with a Bausch & Lomb brand Spectronic 2000 Model Ultraviolet/Visible Spectroscope at the visible light range of 500 nm after rubbing the lenses and rinsing with isotonic saline. The lenses are then placed in Bausch & Lomb Lensgard ® cases. Each well is filled 2/3 full with isotonic saline solution. A water soluble, non-effervescent tablet from Example I is placed in seven (7) of the lens wells and an effervescent tablet from Example I is placed in the remaining lens well. The cases are closed and shaken to insure dissolution of the tablets. Cases 1–5 containing non-effervescent tablets are placed in Aseptron heat disinfecting units having about a 60 minute cycle with a maximum heating temperature of about 80° C. At the end of the cycle, the lenses are removed, rubbed and rinsed in isotonic saline. Cases 6 and 7 also containing cleaning solution made from non-effervescent tablets and case 8 containing solution from the effervescent tablet are allowed to soak overnight at room temperature. Cases 6–8 are then emptied, filled with distilled water and then placed in Aseptron units for one cycle to disinfect the lenses. At the completion of the cycle the lenses are removed, rubbed and rinsed in isotonic saline. Post cleaning light transmission readings are taken on all the lenses.

TABLE

| Lens | One Step | Two Step | Tablet | Pre-Clean % Transmission | Post-Clean % Transmission |
| --- | --- | --- | --- | --- | --- |
| 1 | X | | Non-Effervescent | 90.5 | 95.6 |
| 2 | X | | Non-Effervescent | 90.3 | 95.1 |
| 3 | X | | Non-Effervescent | 80.7 | 96.1 |
| 4 | X | | Non-Effervescent | 92.8 | 94.8 |
| 5 | X | | Non-Effervescent | 84.0 | 95.1 |
| 6 | | X | Non-Effervescent | 84.4 | 94.1 |
| 7 | | X | Non-Effervescent | 76.1 | 96.2 |
| 8 | | X | Effervescent | 85.7 | 97.3 |

A lens post clean light transmission of 94 percent or more is considered cosmetically clean. Accordingly, the data in the table demonstrates the single-step cleaning and disinfecting method performs favorably against the conventional two step method.

While the invention has been described in conjunction with specific examples thereof, this is illustrative only. Accordingly, many alternatives, modifications and variations will be apparent to those skilled in the art in light of the foregoing description, and it is therefore intended to embrace all such alternatives, modifications and variations as to fall within the spirit and broad scope of the appended claims.

What is claimed is:

1. A single step method for simultaneously (1) cleaning contact lenses of proteinaceous and other deposits using a proteolytic enzyme in aqueous solution, and (2) disinfecting the contact lenses, comprising placing the lenses in a solution comprising a proteolytic enzyme dissolved in water at about room temperature and then heating the solution and lenses to an elevated temperature of more than 60° C. and less than 100° C. for a period of time of 60 minutes or less, sufficient to clean and disinfect the lenses.

2. The method of claim 1 wherein the period of time for which the solution and lenses are heated to an elevated temperature is 20 minutes or less.

3. The method of claim 1 wherein the period of time for which the solution and lenses are heated to an elevated temperature is between 5 minutes and 15 minutes.

4. The method of claim 1 wherein the enzyme solution contains papain.

5. The method of claim 1 wherein the enzyme solution contains pancreatin.

6. The method of claim 1 wherein the contact lenses are soft contact lenses.

7. A single step method for simultaneously (1) cleaning contact lenses of proteinaceous and other deposits using a proteolytic enzyme in aqueous solution, (2) disinfecting the contact lenses, and (3) deactivating the enzyme, comprising placing the lenses in a solution comprising a protease dissolved in water at about room temperature and then heating the solution and lenses to an elevated temperature of more than 60° C. and less than 100° C. for a period of time of 60 minutes or less sufficient to clean and disinfect the lenses and denature the protease.

8. The method of claim 7 wherein the period of time for which the solution and lenses are heated to an elevated temperature is 20 minutes or less.

9. The method of claim 7 wherein the period of time for which the solution and lenses are heated to an elevated temperature is between 5 minutes and 15 minutes.

10. The method of claim 7 wherein the enzyme solution contains papain.

11. The method of claim 7 wherein the enzyme solution contains pancreatin.

12. The method of claim 7 wherein the protease-containing solution includes amylase.

13. The method of claim 12 wherein the amylase is a microbial amylase.

14. The method of claim 7 wherein the protease is derived from a Bacillus or Streptomyces bacteria or an Aspergillus mold.

15. The method of claim 14 wherein the protease is derived from *B. subtilis*.

16. The method of claim 7 wherein the elevated temperature is more than 60° C. and less than 85° C.

17. The method of claim 16 wherein the elevated temperature is between 65° C. and 75° C.

18. The method of claim 7 wherein the contact lenses are of the extended-wear type having a water content of at least 55% by weight.

19. The method of claim 7 wherein the solution is substantially isotonic with lacrimal fluids.

20. The method of claim 7 wherein the heating of the lenses and solution to an elevated temperature is followed by cooling of the solution and lenses.

21. A single step method for simultaneously (1) cleaning contact lenses of proteinaceous and other deposits using a microbial-derived proteolytic enzyme in aqueous solution, and (2) disinfecting the contact lenses, comprising placing the lenses in a solution comprising a microbial-derived proteolytic enzyme dissolved in water at about room temperature and then heating the solution and lenses to an elevated temperature of more than 60° C. and less than 100° C. for a period of time of 60 minutes or less, sufficient to clean and disinfect the lenses.

22. A single step method for simultaneously (1) cleaning contact lenses of proteinaceous and other deposits using an activator-free microbial-derived proteolytic enzyme in aqueous solution, and (2) disinfecting the contact lenses, comprising placing the lenses in an activator-free solution comprising an activator-free microbial-derived proteolytic enzyme dissolved in water at about room temperature and then heating the solution and lenses to an elevated temperature of more than 60° C. and less than 100° C. for a period of time of 60 minutes or less, sufficient to clean and disinfect the lenses.

23. A single step method for simultaneously (1) cleaning contact lenses of proteinaceous and other deposits using a proteolytic enzyme derived from a Bacillus or Streptomyces bacteria or an Aspergillus mold in aqueous solution, and (2) disinfecting the contact lenses, comprising placing the lenses in a solution comprising a proteolytic enzyme derived from a Bacillus or Streptomyces bacteria or an Aspergillus mold dissolved in water at about room temperature and then heating the solution and lenses to an elevated temperature of more than 60° C. and less than 100° C. for a period of time of 60 minutes or less, sufficient to clean and disinfect the lenses.

24. A single step method for simultaneously (1) cleaning contact lenses of proteinaceous and other deposits using an activator-free proteolytic enzyme derived from a Bacillus or Streptomyces bacteria or an Aspergillus mold in aqueous solution, and (2) disinfecting the contact lenses, comprising placing the lenses in an activator-free solution comprising an activator-free proteolytic enzyme derived from a Bacillus or Streptomyces bacteria or an Aspergillus mold dissolved in water at about room temperature and then heating the solution and lenses to an elevated temperature of more than 60° C. and less than 100° C. for a period of time of 60 minutes or less, sufficient to clean and disinfect the lenses.

25. A single step method for simultaneously (1) cleaning contact lenses of proteinaceous and other deposits using a proteolytic enzyme derived from *B. subtilis* in aqueous solution, and (2) disinfecting the contact lenses, comprising placing the lenses in a solution comprising a proteolytic enzyme derived from *B. subtilis* dissolved in water at about room temperature and then heating the solution and lenses to an elevated temperature of more than 60° C. and less than 100° C. for a period of time of 60 minutes or less, sufficient to clean and disinfect the lenses.

26. A single step method for simultaneously (1) cleaning contact lenses of proteinaceous and other deposits using an activator-free proteolytic enzyme derived from *B. subtilis* in aqueous solution, and (2) disinfecting the contact lenses, comprising placing the lenses in an activator-free solution comprising an activator-free proteolytic enzyme derived from *B. subtilis* dissolved in water at about room temperature and then heating the solution and lenses to an elevated temperature of more than 60° C. and less than 100° C. for a period of time of 60 minutes or less, sufficient to clean and disinfect the lenses.

* * * * *

UNITED STATES PATENT AND TRADEMARK OFFICE
CERTIFICATE OF CORRECTION

PATENT NO. : 4,614,549
DATED : September 30, 1986
INVENTOR(S) : Lai Ogunbiyi, Thomas M. Riedhammer and Francis X. Smith It is certified that error appears in the above-identified patent and that said Letters Patent are hereby corrected as shown below:

In Column 2 at line 65, delete "B. subtilis" and insert -- B. licheniformis --.

In Column 5 at lines 7 and 8, delete "B. subtilis" and insert -- B. licheniformis --.

In Claim 15, column 7 at line 25, delete "B. subtilis" and insert -- B. licheniformis --.

In Claim 25, column 8 at lines 34 and 37, delete "B. subtilis" and insert -- B. licheniformis --.

In Claim 26, column 8 at lines 46 and 49, delete "B. subtilis" and insert -- B. licheniformis --.

Signed and Sealed this

Seventh Day of April, 1987

Attest:

DONALD J. QUIGG

Attesting Officer     Commissioner of Patents and Trademarks